US008831706B2

(12) United States Patent
Fu et al.

(10) Patent No.: US 8,831,706 B2
(45) Date of Patent: Sep. 9, 2014

(54) FIDUCIAL-LESS TRACKING OF A VOLUME OF INTEREST

(75) Inventors: Dongshan Fu, Santa Clara, CA (US); Kajetan R. Berlinger, Munich (DE)

(73) Assignee: Accuray Incorporated, Sunnyvale, CA (US)

( * ) Notice: Subject to any disclaimer, the term of this patent is extended or adjusted under 35 U.S.C. 154(b) by 1190 days.

(21) Appl. No.: 11/592,772

(22) Filed: Nov. 3, 2006

(65) Prior Publication Data

US 2008/0109013 A1    May 8, 2008

(51) Int. Cl.

| A61B 5/05 | (2006.01) |
| A61B 6/00 | (2006.01) |
| A61N 5/10 | (2006.01) |
| A61B 6/03 | (2006.01) |
| A61B 5/055 | (2006.01) |

(52) U.S. Cl.
CPC .............. *A61B 6/032* (2013.01); *A61B 6/5217* (2013.01); *A61N 5/1049* (2013.01); *A61B 6/4458* (2013.01); *A61N 2005/1062* (2013.01); *A61N 5/1037* (2013.01); *A61B 6/037* (2013.01); *A61B 5/055* (2013.01)
USPC .......... 600/427; 600/407; 600/425; 382/128; 382/131; 382/182; 382/254; 378/65

(58) Field of Classification Search
USPC .......... 600/407, 425, 427; 382/182, 254, 128, 382/131
See application file for complete search history.

(56) References Cited

U.S. PATENT DOCUMENTS

| 5,117,829 | A | * | 6/1992 | Miller et al. ................... 600/427 |
| 5,207,223 | A | | 5/1993 | Adler | |
| 6,307,914 | B1 | | 10/2001 | Kunieda et al. | |
| 6,560,354 | B1 | * | 5/2003 | Maurer et al. ................. 382/131 |
| 6,711,282 | B1 | * | 3/2004 | Liu et al. ....................... 382/132 |
| 7,260,426 | B2 | | 8/2007 | Schweikard et al. | |
| 7,327,865 | B2 | | 2/2008 | Fu et al. | |
| 7,853,308 | B2 | * | 12/2010 | Sauer et al. ................... 600/425 |
| 2004/0092815 | A1 | * | 5/2004 | Schweikard et al. ......... 600/425 |
| 2005/0053267 | A1 | | 3/2005 | Mostafavi | |
| 2006/0002615 | A1 | | 1/2006 | Fu et al. | |
| 2006/0074292 | A1 | | 4/2006 | Thomson et al. | |

FOREIGN PATENT DOCUMENTS

EP    1542165    6/2005

OTHER PUBLICATIONS

PCT International Preliminary Report on Patentability, PCT/US2007/021620 filed Oct. 9, 2007, mailed May 14, 2009.
PCT International Search Report and Written Opinion of the International Searching Authority, PCT/US07/21620 filed Oct. 9, 2007, mailed May 9, 2008.

(Continued)

*Primary Examiner* — Unsu Jung
*Assistant Examiner* — Joseph M Santos Rodriguez
(74) *Attorney, Agent, or Firm* — Lowenstein Sandler LLP

(57) ABSTRACT

A method and an apparatus for fiducial-less tracking of a volume of interest (VOI) have been presented. In some embodiments, a pair of intra-operative images of a portion of a patient is generated during treatment of a target region in the patient to show a bony structure of the patient. The bony structure shown is movable responsive to respiration of the patient. Then the pair of intra-operative images is compared with a set of digitally reconstructed radiograph (DRR) pairs, generated from volumes of four-dimensional (4D) diagnostic imaging data, to determine a location of the movable bony structure that corresponds to a particular volume of the 4D diagnostic imaging data.

14 Claims, 11 Drawing Sheets

(56) References Cited

OTHER PUBLICATIONS

Coste-Manière, È., "Robotic whole body stereotactic radiosurgery: clinical advantages of the CyberKnife® integrated system", The International Journal of Medical Robotics +Computer Assisted Surgery, 2005, www.roboticpublications.com, pp. 28-39.

Paul J. Keall et al., "Four-dimensional radiotherapy planning for DMLC-based respiratory motion tracking", Med. Phys. 32 (4), Apr. 2005, pp. 942-951.

Paul Keall, "4-Dimensional Computed Tomography Imaging and Treatment Planning", Seminars in Radiation Oncology, vol. 14, No. 1 (Jan. 2004): pp. 81-90.

Rietzel et al., Four-Dimensional Image-Based Treatment Planning: Target Volume Segmentation and Dose Calculation in the presence of Respiratory Motion, International Journal of Radiation Oncology Biology and Physics, vol. 61, Issue 5, Apr. 1, 2005, pp. 1535-1550.

A. Schweikard, G. Glosser, M. Bodduluri, M. Murphy, J. A. Adler, "Robotic motion compensation for respiratory movement during radiosurgery," Special Issue on Planning and Image-guided in Radiation Therapy, Computer-Aided Surgery, Sep. 2000, pp. 263-277.

* cited by examiner

FIDUCIAL-LESS TRACKING OF A VOLUME OF INTEREST

TECHNICAL FIELD

The present invention relates generally to radiosurgery. More particularly, this invention relates to fiducial-less tracking of a volume of interest (VOI).

BACKGROUND

Radiosurgery, also referred to as radiation treatment, typically involves delivery of a predetermined dosage of radiation to a target region in a patient to treat a tumor within the target region. Typically, a high dosage of radiation is delivered to the target region while the rest of the patient's body may be exposed to a relatively low level of radiation. If a high dosage of radiation is mistakenly delivered outside of the target region, not only the tumor may not be treated properly, healthy tissue outside of the target region may be damaged by the mistakenly delivered radiation. Thus, accurate determination of the location of the target region during treatment delivery is crucial in providing safe and effective radiation treatment to the patient. The location of the target region during treatment delivery may also be referred to as the intra-operative location of the target region in the following discussion.

Although a patient undergoing radiation treatment may be substantially immobilized, there are nevertheless movements of the patient caused by respiration of the patient. Such movements are particularly significant in certain parts of the patient's body, such as the lungs, the diaphragm, etc., such that the accuracy in radiation delivery to a target region within these parts may be affected. In order to accurately track the location of a target region that moves responsive to respiration, various techniques have been developed, including irradiation during breath-hold, gating techniques, and active tracking of the target region.

Irradiation during breath-hold requires the patient undergoing radiosurgery to hold his/her breath in a particular way. Typically, the patient has to be trained by verbal commands in order to achieve nearly full vital capacity during breath-hold. However, the above technique is complicated and inconvenient to the patient because training is required. Further, the above technique is susceptible to error because the patient may easily miss a verbal command, and thus, unintentionally changing the duration of the breath-hold. Alternatively, the patient may breathe through a mouthpiece connected to a portable system for coordinating treatment with the patient's respiration. The system may measure the lung volume and display relevant data on a monitor. If the pre-specified breathing volume is reached, a valve blocks airflow for a predefined time span. Irradiation is performed during breath-hold. Many patients can tolerate a breath-hold of about ten to thirty seconds. Although training may not be required under this approach, nevertheless, it is still uncomfortable for the patient to hold his/her breath repeatedly during treatment.

Another conventional fiducial-less radiosurgical technique is gating. To implement gating, one or more sensors, which may include sensors internal and/or external to the patient's body, collect information about the current state of the respiration of the patient. Each time a target region moves out of a predefined window of a particular sensor, the radiation source is switched off. Although gating may be more comfortable for the patient than irradiation during breath-hold, the treatment time of gating may significantly increase due to interruption of treatment caused by frequent switching off of the radiation source.

Active tracking of the target region is another conventional fiducial-less radiation treatment technique. When the target region moves away from a predetermined location, instead of switching of the radiation source, the direction and/or location of the radiation source is adjusted so that the radiation beam substantially moves with the target region. Thus, the location of the target region has to be tracked during treatment. Conventionally, fiducials are used to track the location of the target region during treatment.

Fiducial is a term derived from surveying, meaning a reference marker. Here, a fiducial is a radio opaque marker that is visible to an imaging system of the treatment delivery system. Fiducials may be attached to or implanted into a patient's body to allow surgeons to track the intra-operative location of the target region during treatment delivery.

However, fiducial-based tracking may be undesirable for patients because of various reasons. It is typically uncomfortable for the patients to have fiducials implanted into their bodies. Further, complications may result from the implantation of fiducials. Although attaching fiducials to a patient's skin may be easier and more comfortable for the patient and less risky, the accuracy in tracking the volume of interest in the patient's body may be compromised because the fiducials attached are farther away from the target region and thus, the intra-operative movement of the fiducials and/or intra-operative locations of the fiducials may not correlate well with the intra-operative locations of the target region.

BRIEF DESCRIPTION OF THE DRAWINGS

The present invention is illustrated by way of example and not limitation in the figures of the accompanying drawings in which like references indicate similar elements.

DETAILED DESCRIPTION

Embodiments of fiducial-less tracking of a volume of interest (VOI) are described herein. In the following description, numerous details are set forth to provide a more thorough explanation of embodiments of the present invention. It will be apparent, however, to one skilled in the art, that embodiments of the present invention may be practiced without these specific details. In other instances, well-known structures and devices are shown in block diagram form, rather than in detail, in order to avoid obscuring embodiments of the present invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification do not necessarily all refer to the same embodiment.

In some embodiments, a pair of intra-operative images of a portion of a patient is generated during treatment of a target region in the patient to show a bony structure of the patient. The bony structure shown is movable responsive to respiration of the patient. Then the pair of intra-operative images is compared with a set of digitally reconstructed radiograph (DRR) pairs, generated from four-dimensional (4D) diagnostic imaging data, to determine a location of the movable bony structure that corresponds to a particular volume of the 4D diagnostic imaging data in order to track the intra-operative location of the target region. As such, no fiducial markers have to be implanted into the patient's body in order to track the intra-operative location of the target region even though the target region may move responsive to the respiration of the patient.

In the following discussion, a target region may include an anatomical feature(s) of a patient such as a pathological or normal anatomy and may include one or more non-anatomical reference structures. Alternatively, a target region may not include an anatomical structure in embodiments outside the field of medical diagnostic imaging and patient treatment. Furthermore, a VOI herein refers to a predetermined volume in a body of a patient, which may or may not overlap with the target region. The VOI may include a static bony structure (e.g., portions of a spine), which remains substantially static as the patient breathes, and/or a bony structure movable responsive to respiration of the patient (e.g., portions of a rib cage).

Figure 1:
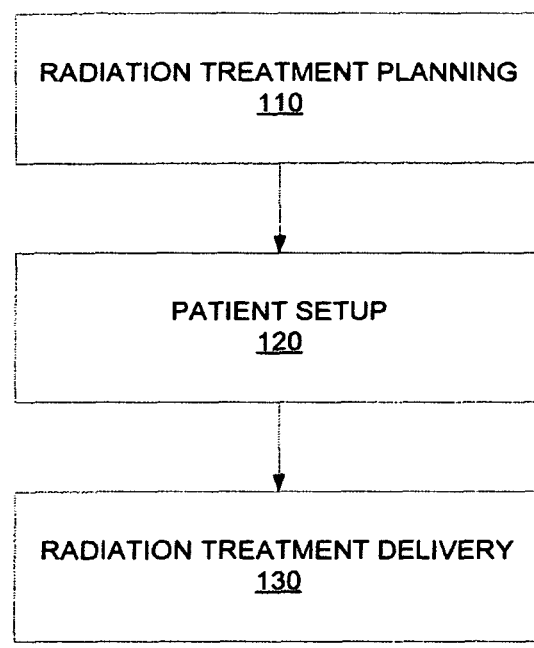
FIG. 1 illustrates one embodiment of a process to perform radiosurgery.

FIG. 1 illustrates one embodiment of a process to perform radiosurgery. The process is performed by processing logic that may comprise hardware (e.g., circuitry, dedicated logic, etc.), software (such as is run on a general-purpose computer system, a link device, or a dedicated machine), firmware, or a combination of any of the above.

Referring to FIG. 1, processing logic performs radiation treatment planning to prepare for treatment delivery to a target region in a patient's body (processing block 110). Then the patient is setup in block 120. In some embodiments, the patient setup includes registering at least a portion of the spine of the patient to globally align the patient. To register the portion of the spine, processing logic may determine the spatial transform that maps points on the DRR pair showing the spine to corresponding points in a pair of x-ray images of the spine captured during patient setup. The patient may lie on a treatment couch. Based on the spine registration, a position of the treatment couch and/or the patient may be adjusted accordingly. After setting up the patient, processing logic delivers radiation treatment to the target region, such as a tumor in the lung of the patient, a tumor in the liver of the patient, etc. (processing block 130). Details of treatment planning and treatment delivery are explained with reference to various embodiments described below.

Figure 2A:
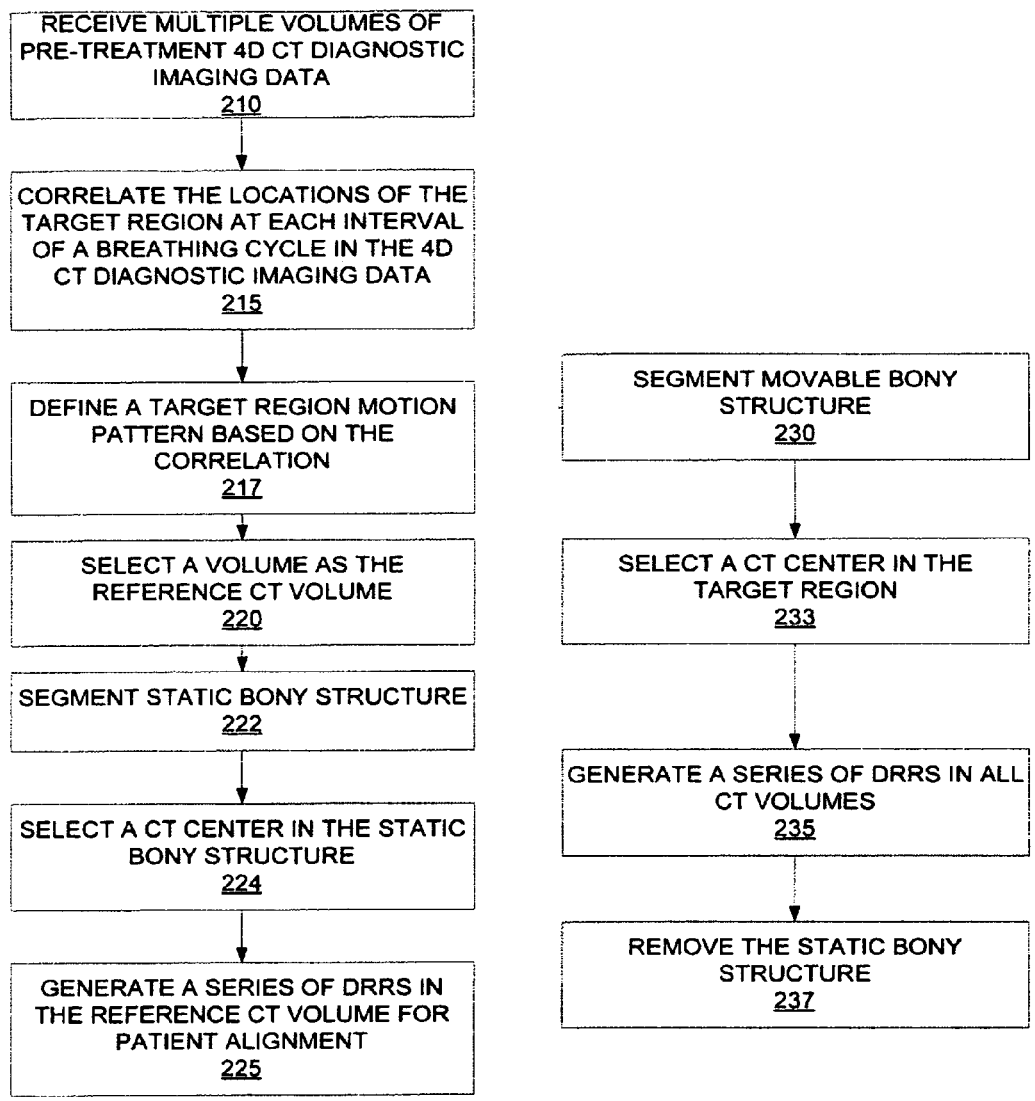
FIG. 2A illustrates one embodiment of a process to plan for radiosurgery.

FIG. 2A illustrates one embodiment of a process to plan for radiosurgery, which may also be referred to as a treatment planning process. The process is performed by processing logic that may comprise hardware (e.g., circuitry, dedicated logic, etc.), software (such as is run on a general-purpose computer system, a link device, or a dedicated machine), firmware, or a combination of any of the above.

Referring to FIG. 2A, processing logic receives multiple volumes of pre-treatment four-dimensional (4D) computerized tomography (CT) diagnostic imaging data, also referred to as 4D CT scan data (processing block 210). In general, CT is the computerized generation of a multi-dimensional image by interpreting several radiographs of an object taken from different directions. Alternatively, processing logic may receive other types of 4D diagnostic imaging data captured by other types of medical imaging techniques, such as magnetic resonance imaging (MRI), positron emission tomography (PET) scan, ultrasonic scan, single photo emission computed tomography (SPECT), etc. The 4D diagnostic imaging data may be imported into a treatment planning system or may already reside on a diagnostic CT imaging system that is also used for treatment planning system that was used to perform the diagnostic 4D CT imaging. The treatment planning system may be fully compliant with Digital Imaging and Communications in Medicine (DICOM) standards for the distribution and viewing of medical images and the DICOM-RT standard for viewing radiotherapy information overlain on medical images.

Figure 2B:
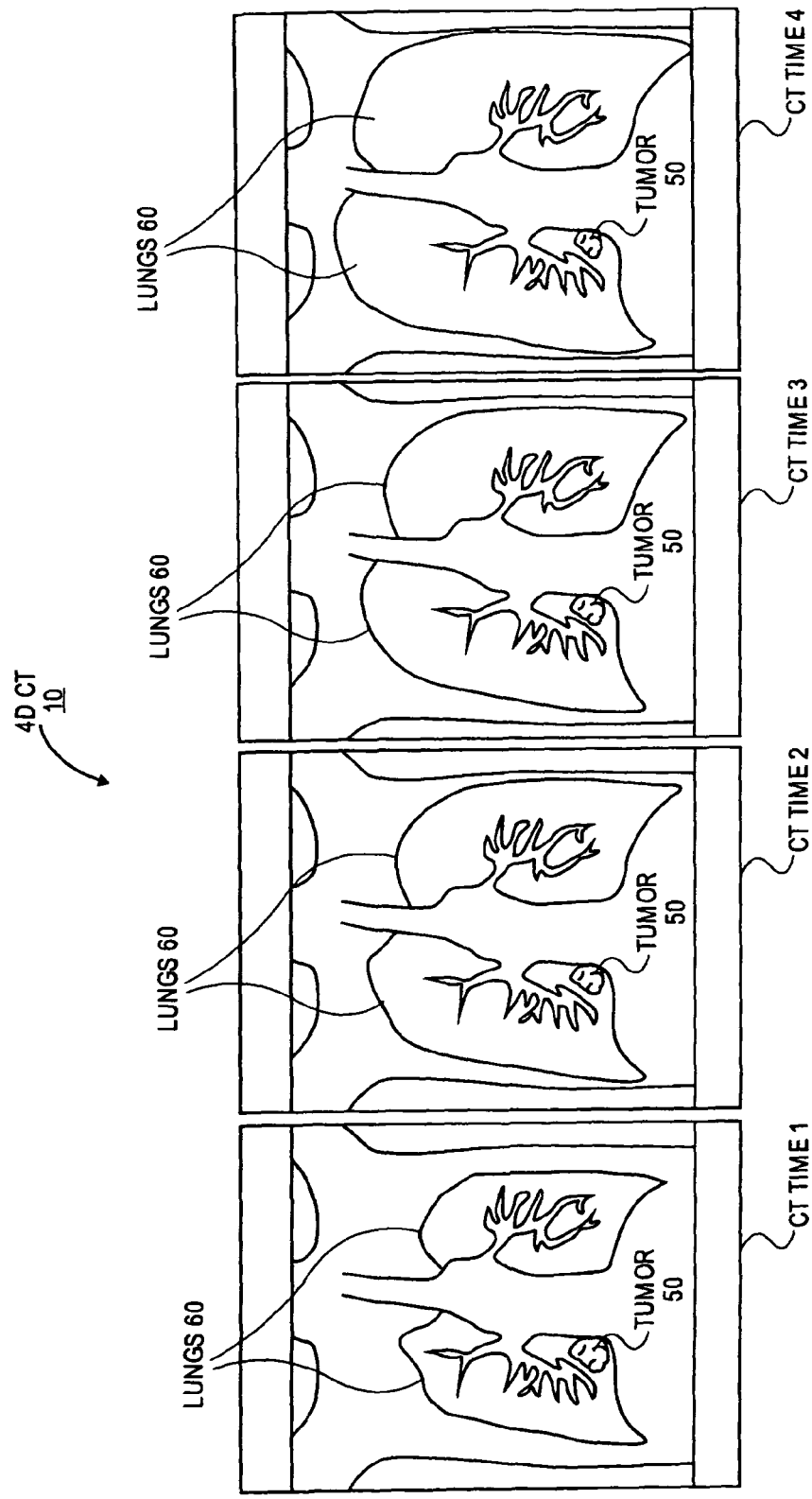
FIG. 2B is a conceptual illustration of one embodiment of a 4D CT scan.

It should be noted that the four dimensions refer to three spatial dimensions and one temporal dimension, as opposed to four spatial dimensions. More specifically, the 4D CT scan data is a collection of three-dimensional (spatial) images, with each of the three dimensional (3D) images taken at a different point in time in a motion cycle (e.g., during the respiratory cycle, cardiac cycle, artery pulsation, etc. of a patient) with known temporal relationship. FIG. 2B is a conceptual illustration of a 4D CT scan of a patient's chest region including lungs 60 and a target tumor 50. The exemplary 4D CT scan 10 of FIG. 2B includes four 3D CTs taken a four time points in the patient's respiratory cycle: CT Time 1, CT Time 2, CT Time 3 and CT Time 4. Each of the 3D CT scans has an index associated with it describing a subset of the respiratory cycle, for example, splitting the cycle into index 0 (time 1)=full exhale, index 100 (time 4)=full inhale and two intermediate indexes for time 2 and time 3. As can be seen from an inspection of the images in FIG. 2B, tumor 50 is, for this example, displaced and deformed in the CT image at time 4, full inhale, relative to its positions and shape at full exhale in CT image at time 1.

In one embodiment, the 4D CT scan data may be generated using a 4D CT scanner, for example, a 4D CT scanner produced by General Electric Company. Alternatively, other 4D CT scanners may be used. A 4D CT scanner includes a device, such as a spirometer, strain gauge, optical tracker, etc., that is configured to take instantaneous measurements of the patient's position in the respiratory cycle. When a slice is acquired, the current respiratory measurement position is recorded. This measurement is used to place the CT slice in one of the 3D CT scans with the index closest to the given measurement of the respiratory cycle. While with 3D CT scans, some subsets of slices may be acquired simultaneously, there is not attempt to index the timing of the slice acquisition to physical processes, e.g., the breathing cycle, other than in optionally halting the breathing cycle by instructing the patient to cease breathing while the scan is taken.

The 4D CT scan data may be acquired in a single motion cycle, or may be acquired over multiple motion cycles. In some embodiments, a breathing cycle is defined for the patient, which may be divided into a number of substantially evenly spaced time intervals or points. The 4D CT scan data may be captured at different intervals of the breathing cycle of the patient. Specifically, two or more conventional 3D CT images may be acquired during breath-hold at different points in the breathing cycle (e.g., at end inspiration and end expiration). Accordingly, the term 4D CT scan data may be used herein to mean a set of two or more 3D images that represent different time points in a motion cycle regardless of the method of acquiring the scan data.

In some embodiments, the multiple volumes of pre-treatment 4D CT diagnostic imaging data may indicate location of a target region in a patient's body (e.g., a lung tumor, a liver tumor, etc.). The multiple volumes of pre-treatment 4D CT diagnostic imaging data may further include volumes of 4D diagnostic imaging data of a VOI in the patient's body having rich bony structure movable responsive to respiration of the patient (e.g., a portion of the patient's a rib cage). The VOI may also include a static bony structure that remains substantially static when the patient breathes (e.g., the spine of the patient). Note that the target region and the VOI may or may not overlap, partially or substantially.

Referring back to FIG. 2A, processing logic correlates the locations of the target region at each interval of the breathing cycle in the 4D CT diagnostic imaging data (processing block 215). Based on the correlation, processing logic may define a target region motion pattern (processing block 217).

In some embodiments, processing logic selects a volume out of the multiple volumes of pre-treatment 4D CT diagnostic imaging data to be a reference volume (processing block 220). Then processing logic may segment a static bony structure in the volumes of 4D CT diagnostic imaging data (processing block 222). Segmentation in general is the partition of an image or data of an image into one or more regions according to at least one predetermined criterion. Details of one embodiment of segmentation are described below. After segmenting the static bony structure, processing logic may select a CT center in the static bony structure (processing block 224). Then processing logic generates a series of two-dimensional (2D) images in the reference volume for global patient alignment (processing block 225). In some embodiments, the 2D images include digitally reconstructed radiographs (DRRs), which are synthetic x-ray images generated from a CT volume by volume rendering.

In some embodiments, processing logic segments a movable bony structure in the volumes of 4D CT diagnostic imaging data (processing block 230). Then processing logic may select a CT center in the target region (processing block 233). Processing logic may generate a series of 2D images, such as DRRs, for all the volumes of 4D CT diagnostic imaging data (processing block 235). Then processing logic may remove the static bony structure from the 2D images (processing block 237). Without the static bony structure obstructing the view of the movable bony structure in the 2D images, the movable bony structure in the 2D images may be more clearly visible, and thus, making it easier to compare the 2D images with other images of the movable bony structure.

Figure 2C:
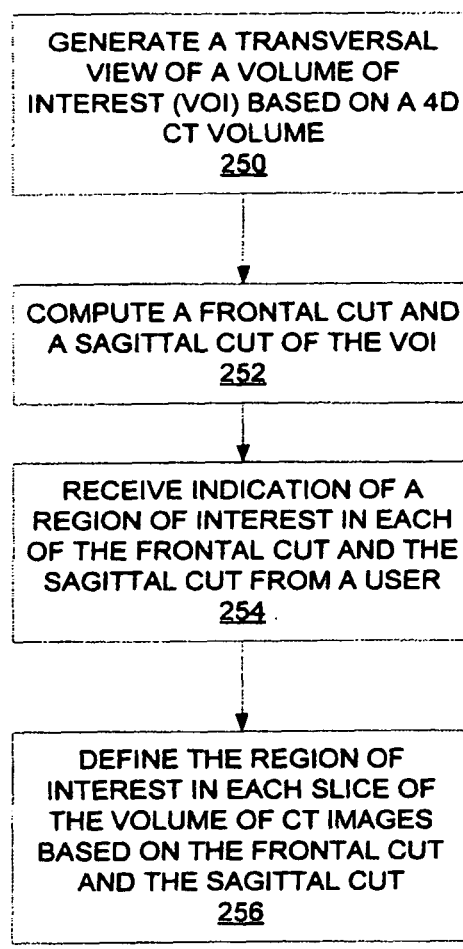
FIG. 2C illustrates one embodiment of a process to segment static bony structure.

FIG. 2C illustrates one embodiment of a process to segment a VOI in a 4D CT volume of diagnostic imaging data, which includes a set of 4D CT slices. The VOI may include a static bony structure (e.g., part of a spine), a movable bony structure (e.g., part of a rib cage), etc. The process is performed by processing logic that may comprise hardware (e.g., circuitry, dedicated logic, etc.), software (such as is run on a general-purpose computer system, a link device, or a dedicated machine), firmware, or a combination of any of the above.

Referring to FIG. 2C, processing logic generates a transversal view of the VOI based on the 4D CT volume (processing block 250). Then processing logic computes two orthogonal cuts, namely, a frontal cut and a sagittal cut, of the VOI (processing block 252). In some embodiments, processing logic provides a graphical user interface (GUI) to allow a user to select a point to define the two orthogonal cuts. In some embodiments, processing logic may generate thick orthogonal slices by adding the information of the neighboring cuts to the center cut (a.k.a., the original cut) of the respective orthogonal cut. In some embodiments, the user defines the thickness of the cut as well.

In some embodiments, processing logic may receive user input indicating a rough contour of the VOI in each of the orthogonal cuts (processing block 254). Processing logic may generate a GUI to allow the user to enter the input. For example, processing logic may generate two windows, one to display the frontal cut and the other one to display the sagittal cut. A user may draw a polygon surrounding the VOI in each of the orthogonal cuts in the respective window.

Finally, processing logic may define the VOI in each slice of the 4D CT volume based on the user's input on the frontal cut and the sagittal cut (processing block 256). In one embodiment, the VOI is surrounded by a rectangle in every slice, where the abscissas of the rectangle are defined by the frontal cut and the ordinates of the rectangle are defined by the sagittal cut. Processing logic may generate a contour of the VOI using a logical tube defined by these rectangles on the slices. For DRR generation, if a point of interest is located between two consecutive slices, the point of interest may be located by linear interpolation of the corresponding rectangles.

Figure 3:
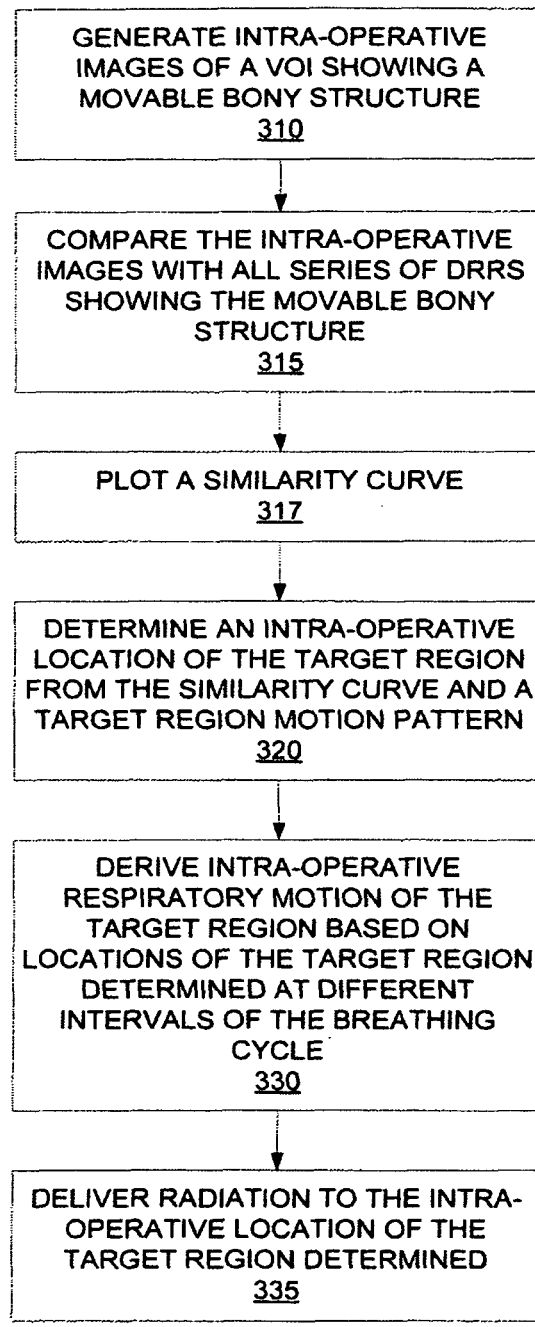
FIG. 3 illustrates one embodiment of a process to delivery radiation treatment.

FIG. 3 illustrates one embodiment of a process to deliver radiation treatment. The process is performed by processing logic that may comprise hardware (e.g., circuitry, dedicated logic, etc.), software (such as is run on a general-purpose computer system, a link device, or a dedicated machine), firmware, or a combination of any of the above.

In some embodiments, processing logic generates intra-operative images of a VOI showing a bony structure movable responsive to respiration of a patient (processing block 310). The movable bony structure may include at least a portion of a rib cage of the patient. In some embodiments, the intra-operative images may include one or more pairs of x-ray images generated by a pair of x-ray imaging modules arranged at a predetermined angle relative to a treatment couch on which the patient lies. Then processing logic compares the intra-operative images with a set of DRR pairs generated from a series of 4D CT volumes showing the movable bony structure (processing block 315). Details of some embodiments of the generation of the DRR pairs from 4D CT volumes prior to treatment delivery have been discussed above. By comparing with the DRR pairs, processing logic may determine similarity between the intra-operative images and the DRR pairs. In some embodiments, processing logic computes a similarity measure value (such as a correlation coefficient) for each DRR pair. Processing logic may plot a similarity curve between the intra-operative images and the DRR pairs (processing block 317).

Figure 9:
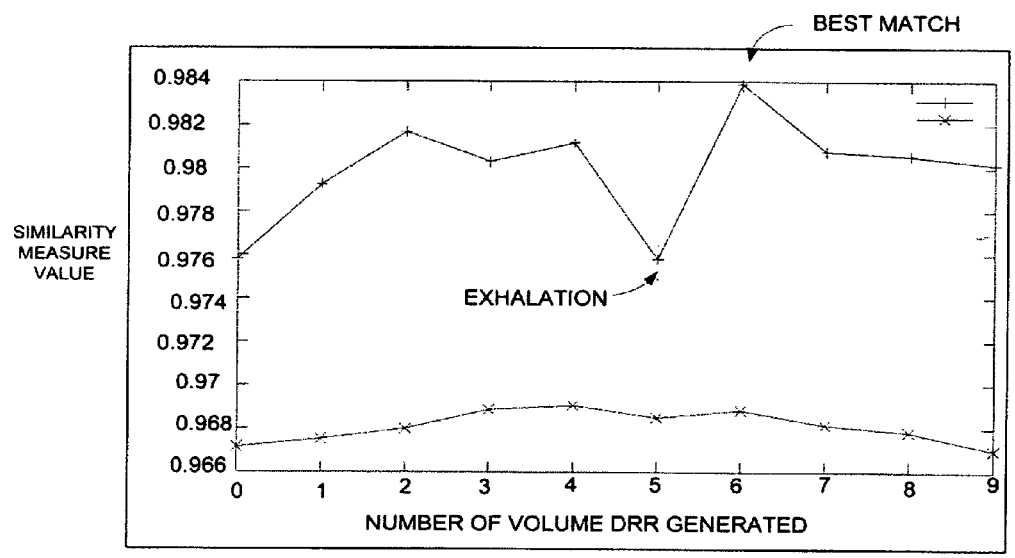
FIG. 9 illustrates one embodiment of a similarity curve.

One embodiment of the similarity curve 900 is illustrated in FIG. 9. Referring to FIG. 9, a similarity measure value is plotted against the number of the 4D CT volume from which a corresponding DRR pair has been generated. The 4D CT volume having the highest similarity measure value is the best match 910.

Referring back to FIG. 3, processing logic then determines an intra-operative location of the target region from the similarity curve and a target region motion pattern (processing block 320). Details of one embodiment of a process to define the target region motion pattern have been discussed above. In some embodiments, processing logic may repeat processing blocks 310, 315, 317, and 320 to determine locations of additional target regions. Furthermore, processing logic may receive external sensor readings (e.g., readings from sensors attached to the patient's skin) and may correlate the external sensor readings with the target region location(s) determined in order to more accurately track the target region during radiation treatment.

In some embodiments, processing logic further derives intra-operative respiratory motion of the target region based on the locations of the target region determined at different intervals of the breathing cycle (processing block 330). Processing logic may compensate the intra-operative locations of the target region determined above by the intra-operative respiratory motion of the target region derived to improve the accuracy of the target region tracking.

Finally, processing logic delivers a predetermined dosage of radiation to the intra-operative location of the target region determined (processing block 335). By correlating locations of the movable bony structure with the target region, the location of the target region may be tracked more accurately because both the movable bony structure and the target region move in response to the respiration of the patient. Furthermore, fiducials are not implanted or attached to the patient's body for tracking the target region according to the above approach. As discussed above, implanting and/or attaching fiducials to the patient may cause discomfort and risk to the patient. Therefore, using the above target region tracking approach in radiation treatment makes it more comfortable and less risky for the patient. Moreover, the procedures of setting up the patient prior to delivering radiation treatment may be simplified as well without having to implant and/or attach fiducials to the patient.

Figure 4:
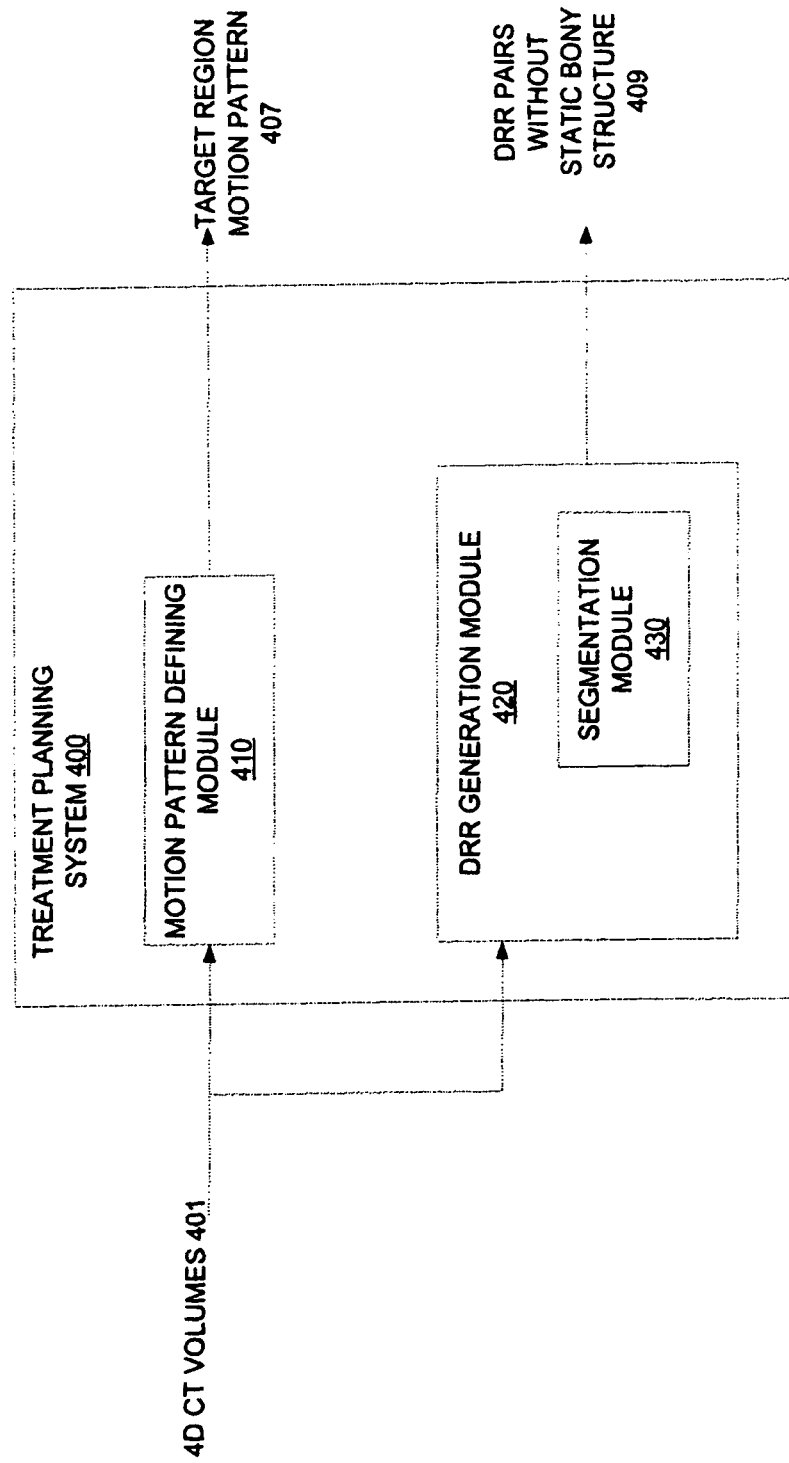
FIG. 4 illustrates a functional block diagram of one embodiment of a radiation treatment planning system.

FIG. 4 illustrates a functional block diagram of one embodiment of a treatment planning system. The treatment planning system 400 includes a motion pattern defining module 410 and a DRR generation module 420 having a segmentation module 430. In some embodiments, multiple 4D CT volumes 401 of a target region in a patient are input to the treatment planning system 400. The 4D CT volumes 401 include 4D CT diagnostic imaging data of the target region. Alternatively, volumes of 4D diagnostic imaging data captured by other imaging techniques (e.g., PET scan, ultrasonic scan, MRI, etc.) may be input to the treatment planning system 400 instead. The target region may be a region in the patient's body that needs radiation treatment, such as a lung tumor, a liver tumor, etc.

In some embodiments, the motion pattern defining module 410 receives the 4D CT volumes 401. Note that as the patient breathes, the target region may move in response to the breathing. Thus, to accurately determine the location of the target region, the motion responsive to the patient's respiration has to be accounted for. In one embodiment, a breathing cycle is defined for the patient, which may include a number of substantially evenly spaced time intervals. The motion pattern defining module 410 then defines a motion pattern 407 of the target region by correlating and interpolating the locations of the target region at each interval in the breathing cycle of the patient.

In addition to the motion pattern defining module 410, the treatment planning system 400 further includes the DRR generation module 420. In some embodiments, the DRR generation module 420 selects a CT volume out of the 4D CT volumes 401 to be a reference CT volume. The DRR generation module 420 may include a segmentation module 430. The segmentation module 430 may segment a static bony structure (e.g., a portion of a spine of the patient) in the 4D CT volumes. The DRR generation module 420 may further select a CT center in the static bony structure. Then the DRR generation module 420 generates a series of DRRs in the reference CT volume for global patient alignment. For example, during patient setup, the series of DRRs generated from the reference CT volume may be used to register the spine of the patient in order to globally align the patient.

In some embodiments, the segmentation module 430 may segment bony structure movable responsive to respiration of the patient, such as an upper portion of the rib cage of the patient. The DRR generation module 420 may select a CT center in the target region to generate a DRR pair for each of the 4D CT volumes 401. Further, the DRR generation module 420 may remove the segmented static bony structure from the DRR pairs generated 409 so that the movable bony structure may become more clearly visible in the DRR pairs generated 409. As such, the DRR generation module 420 may the output DRR pairs 409 without the static bony structure.

Figure 5:
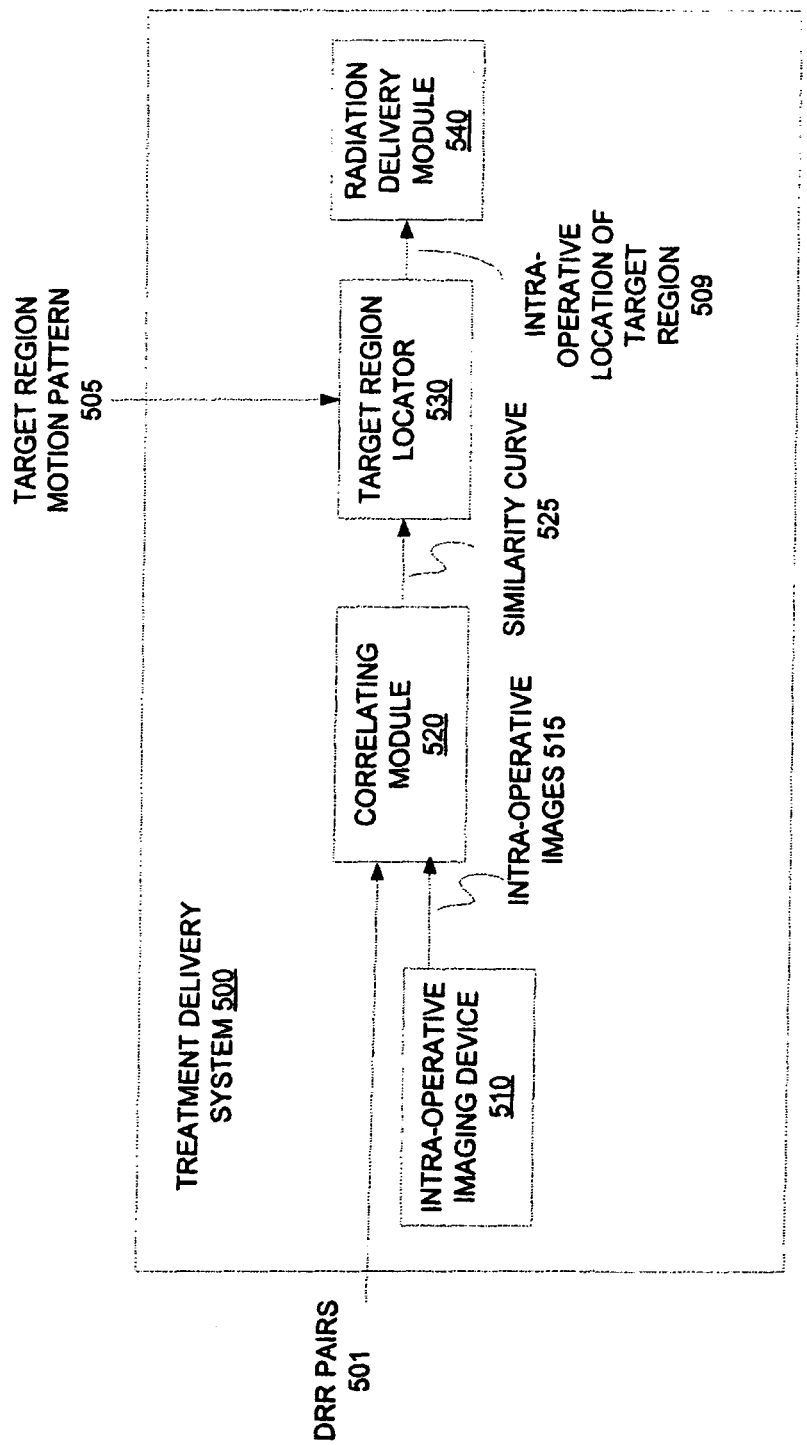
FIG. 5 illustrates a functional block diagram of one embodiment of a radiation treatment delivery system.

FIG. 5 illustrates a functional block diagram of one embodiment of a radiation treatment delivery system. The radiation treatment delivery system 500 includes an intra-operative imaging device 510, a correlating module 520, and a target region locator 530. In some embodiments, the intra-operative imaging device 510 generates intra-operative images 515 of a VOI in a patient to show a bony structure movable responsive to the respiration of the patient. The intra-operative imaging device 510 may include a pair of x-ray imaging modules and the intra-operative images may include a pair of x-ray images of the movable bony structure. The intra-operative images 515 are input to the correlating module 520. The correlating module 520 may also receive a set of DRR pairs 501. Each of the DRR pairs 501 may be generated from a 4D CT volume as described above.

In some embodiments, the correlating module 520 compares the intra-operative images 515 with the DRR pairs 501. Specifically, the correlating module 520 determines how similar the movable bony structure in the intra-operative images 515 and the corresponding movable bony structure in the DRR pairs 501 are. The correlating module 520 may generate a similarity curve 525 based on the comparison, such as the one shown in FIG. 9. Details of FIG. 9 have been discussed above. The similarity curve 525 is input to the target region locator 530.

In addition to the similarity curve 525, the target region locator 530 also receives a target region motion pattern 505, which may be generated by the motion pattern defining module 410 in FIG. 4 as discussed above. The target region locator 530 may determine an intra-operative location 509 of the target region from the similarity curve 525 and the target region motion pattern 505. The intra-operative location 509 of the target region is then input to the radiation delivery module 540, which may deliver a predetermined dosage of radiation to the intra-operative location 509 of the target region.

Figure 6:
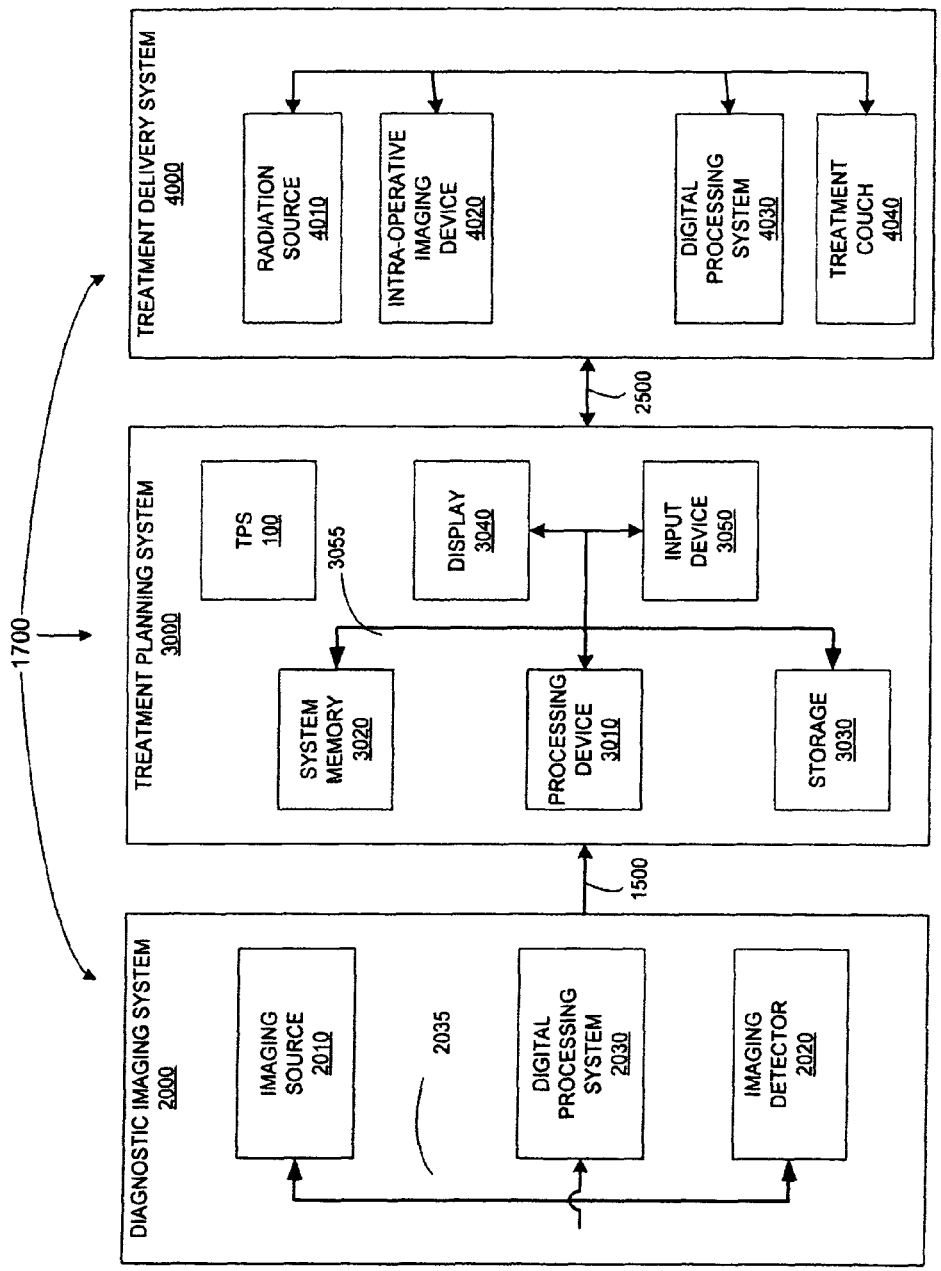
FIG. 6 illustrates one embodiment of a radiosurgical system.

FIG. 6 illustrates one embodiment of a radiation treatment system, a.k.a. radiosurgical system. The depicted treatment system 1700 includes a diagnostic imaging system 2000, a treatment planning system 3000, and a treatment delivery system 4000.

Diagnostic imaging system 2000 is representative of a system capable of producing medical diagnostic images of a VOI that may be used for subsequent diagnosis, treatment planning, and/or treatment delivery. For example, diagnostic imaging system 2000 may be a computed tomography (CT) system, a magnetic resonance imaging (MRI) system, a positron emission tomography (PET) system, an ultrasound system, or the like. For ease of discussion, diagnostic imaging system 2000 is discussed at times in relation to a CT x-ray imaging modality. However, other imaging modalities such as those above may also be used.

Diagnostic imaging system 2000 includes an imaging source 2010 to generate an imaging beam (e.g., x-rays, ultrasonic waves, radio frequency waves, etc.) and an imaging detector 2020 to detect and receive the beam generated by imaging source 2010, or a secondary beam or emission stimulated by the beam from the imaging source (e.g., in an MRI or PET scan). In one embodiment, imaging system 2000 represents a CT scanner. In one embodiment, diagnostic imaging system 2000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used. The imaging detector(s) may be illuminated by the x-ray imaging source. Alternatively, other numbers and configurations of imaging sources and imaging detectors may be used.

The imaging source 2010 and the imaging detector 2020 are coupled to a digital processing system 2030 to control the imaging operation and process image data. Diagnostic imaging system 2000 includes a bus or other means 2035 for transferring data and commands among digital processing system 2030, imaging source 2010 and imaging detector 2020. Digital processing system 2030 may include one or more general-purpose processors (e.g., a microprocessor), special purpose processor such as a digital signal processor (DSP) or other type of device such as a controller or field programmable gate array (FPGA). Digital processing system 2030 may also include other components (not shown) such as memory, storage devices, network adapters and the like. Digital processing system 2030 may be configured to generate scan data of digital diagnostic images in a standard format, such as the DICOM format, for example. In other embodiments, digital processing system 2030 may generate other standard or non-standard digital image formats. Digital processing system 2030 may transmit diagnostic image files (e.g., the aforementioned DICOM formatted files) to treatment planning system 3000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 3000 includes a processing device 3010 to receive and process image data such as the 4D CT data discussed above. Processing device 3010 may represent one or more general-purpose processors (e.g., a microprocessor), special purpose processor such as a digital signal processor (DSP) or other type of device such as a controller or field programmable gate array (FPGA). Processing device 3010 may be configured to execute instructions for performing the operations of the methods discussed herein that, for example, may be loaded in processing device 3010 from storage 3030 and/or system memory 3020.

Treatment planning system 3000 may also include system memory 3020 that may include a random access memory (RAM), or other dynamic storage devices, coupled to processing device 3010 by bus 3055, for storing information and instructions to be executed by processing device 3010. System memory 3020 also may be used for storing temporary variables or other intermediate information during execution of instructions by processing device 3010. System memory 3020 may also include a read only memory (ROM) and/or other static storage device coupled to bus 3055 for storing static information and instructions for processing device 3010.

Treatment planning system 3000 may also include storage device 3030, representing one or more storage devices (e.g., a magnetic disk drive or optical disk drive) coupled to bus 3055 for storing information and data, for example, the 4D CT data discussed above. Storage device 3030 may also be used for storing instructions for performing the treatment planning procedures discussed herein. In some embodiment, storage device 3030 stores instructions for DRR generation. Processing device 3010 may retrieve the instructions and may execute the instructions to implement a DRR generation module, such as the DRR generation module 420 in FIG. 4, and a motion pattern defining module, such as the motion pattern defining module 410 in FIG. 4.

Processing device 3010 may also be coupled to a display device 3040, such as a cathode ray tube (CRT) or liquid crystal display (LCD), for displaying information (e.g., a two-dimensional or three-dimensional representation of the VOI) to the user. An input device 3050, such as a keyboard, may be coupled to processing device 3010 for communicating information and/or command selections to processing device 3010. One or more other user input devices (e.g., a mouse, a trackball or cursor direction keys) may also be used to communicate directional information, to select commands for processing device 3010 and to control cursor movements on display 3040.

It will be appreciated that treatment planning system 3000 represents only one example of a treatment planning system, which may have many different configurations and architectures, which may include more components or fewer components than treatment planning system 3000 and which may be employed with the present invention. For example, some systems often have multiple buses, such as a peripheral bus, a dedicated cache bus, etc. The treatment planning system 3000 may also include MIRIT (Medical Image Review and Import Tool) to support DICOM import (so images can be fused and target regions delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 3000 may share its database (e.g., data stored in storage device 3030) with a treatment delivery system, such as treatment delivery system 4000, so that it may not be necessary to export from the treatment planning system prior to treatment delivery. Treatment planning system 3000 may be linked to treatment delivery system 4000 via a data link 2500, which may be a direct link, a LAN link or a WAN link as discussed above with respect to data link 1500. It should be noted that when data links 1500 and 2500 are implemented as LAN or WAN connections, any of diagnostic imaging system 2000, treatment planning system 3000 and/or treatment delivery system 4000 may be in decentralized locations such that the systems may be physically remote from each other. Alternatively, any of diagnostic imaging system 2000, treatment planning system 3000 and/or treatment delivery system 4000 may be integrated with each other in one or more systems.

Treatment delivery system 4000 includes a therapeutic and/or surgical radiation source 4010 to administer a prescribed radiation dose to a target volume in conformance with a treatment plan. Treatment delivery system 4000 may also include an imaging device 4020 to capture intra-treatment or intra-operative images of a patient volume (including the target volume) for registration and/or correlation with the diagnostic images described above in order to position the patient with respect to the radiation source. The intra-operative imaging device 4020 may include a pair of x-ray imaging modules. Treatment delivery system 4000 may also include a digital processing system 4030 to control radiation source 4010, intra-operative imaging device 4020, and a patient support device such as a treatment couch 4040. Digital processing system 4030 may include one or more general-purpose processors (e.g., a microprocessor), special purpose processor such as a digital signal processor (DSP) or other type of device such as a controller or field programmable gate array (FPGA). Digital processing system 4030 may also include other components (not shown) such as memory, storage devices, network adapters and the like. Digital processing system 4030 may be coupled to radiation source 4010, intra-operative imaging device 4020 and treatment couch 4040 by a bus 4045 or other type of control and communication interface. Further, the digital processing system 4030 may execute instructions to implement the correlating module 520 and the target region locator 530 shown in FIG. 5.

In some embodiments, the intra-operative imaging device 4020 generates intra-operative images of the VOI in the patient during treatment delivery. The intra-operative images are provided to the digital processing system 4030, which also receives DRR pairs from the treatment planning system 3000. By comparing the DRR pairs and the intra-operative images, the digital processing system 4030 determines an intra-operative location of the VOI in the patient's body. Details of some embodiments of a process to determine the intra-operative location of the VOI have been described above.

It should be noted that the described treatment system 1700 is only representative of an exemplary system. Other embodiments of the system 1700 may have many different configurations and architectures and may include fewer or more components.

Figure 7:
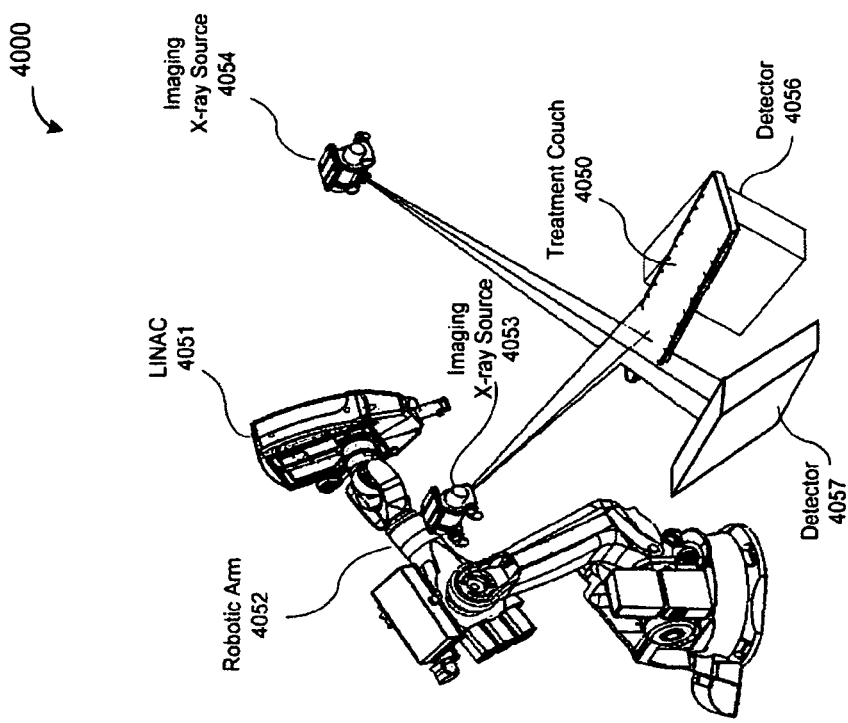
FIG. 7 illustrates one embodiment of a treatment delivery system.

In one embodiment, as illustrated in FIG. 7, treatment delivery system 4000 may be an image-guided, robotic-based radiation treatment delivery system (e.g., for performing radiosurgery) such as the CYBERKNIFE® system developed by Accuray Incorporated of California. FIG. 7 illustrates one embodiment of an image-guided, robotic-based radiation treatment delivery system. In FIG. 7, radiation source 4010 may be represented by a linear accelerator (LINAC) 4051 mounted on the end of a robotic arm 4052 having multiple (e.g., 5 or more) degrees of freedom in order to position the LINAC 4051 to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target region as illustrated in FIG. 9). Treatment can be delivered in either a single session (mono-fraction) or in a small number of sessions as determined during treatment planning. With treatment delivery system 4000, in one embodiment, radiation beams may be delivered according to the treatment plan without fixing the patient to a rigid, external frame to register the intra-operative position of the target volume with the position of the target volume during the pre-operative treatment planning phase.

In FIG. 7, imaging system 4020 may be represented by x-ray sources 4053 and 4054 and x-ray image detectors (imagers) 4056 and 4057. In one embodiment, for example, two x-ray sources 4053 and 4054 may be nominally aligned to project imaging x-ray beams through a patient from two different angular positions (e.g., separated by 90 degrees, 45 degrees, etc.) and aimed through the patient on treatment couch 4050 toward respective detectors 4056 and 4057. In another embodiment, a single large imager can be used that would be illuminated by each x-ray imaging source. Alternatively, other numbers and configurations of imaging sources and imagers may be used.

Digital processing system 4030 may implement algorithms to register images obtained from imaging system 4020 with pre-operative treatment planning images in order to align the patient on the treatment couch 4050 within the treatment delivery system 4000, and to precisely position the radiation source with respect to the target volume.

The treatment couch 4050 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 4050 may be a component of another mechanical mechanism, such as the Axum® treatment couch developed by Accuray Incorporated of California, or be another type of conventional treatment table known to those of ordinary skill in the art.

Alternatively, treatment delivery system 4000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target region. In IMRT planning, the optimization algorithm selects subsets of the main beam and determines the amount of time that the patient should be exposed to each subset, so that the prescribed dose constraints are best met. In one particular embodiment, the gantry based system may have a gimbaled radiation source head assembly.

Figure 8:
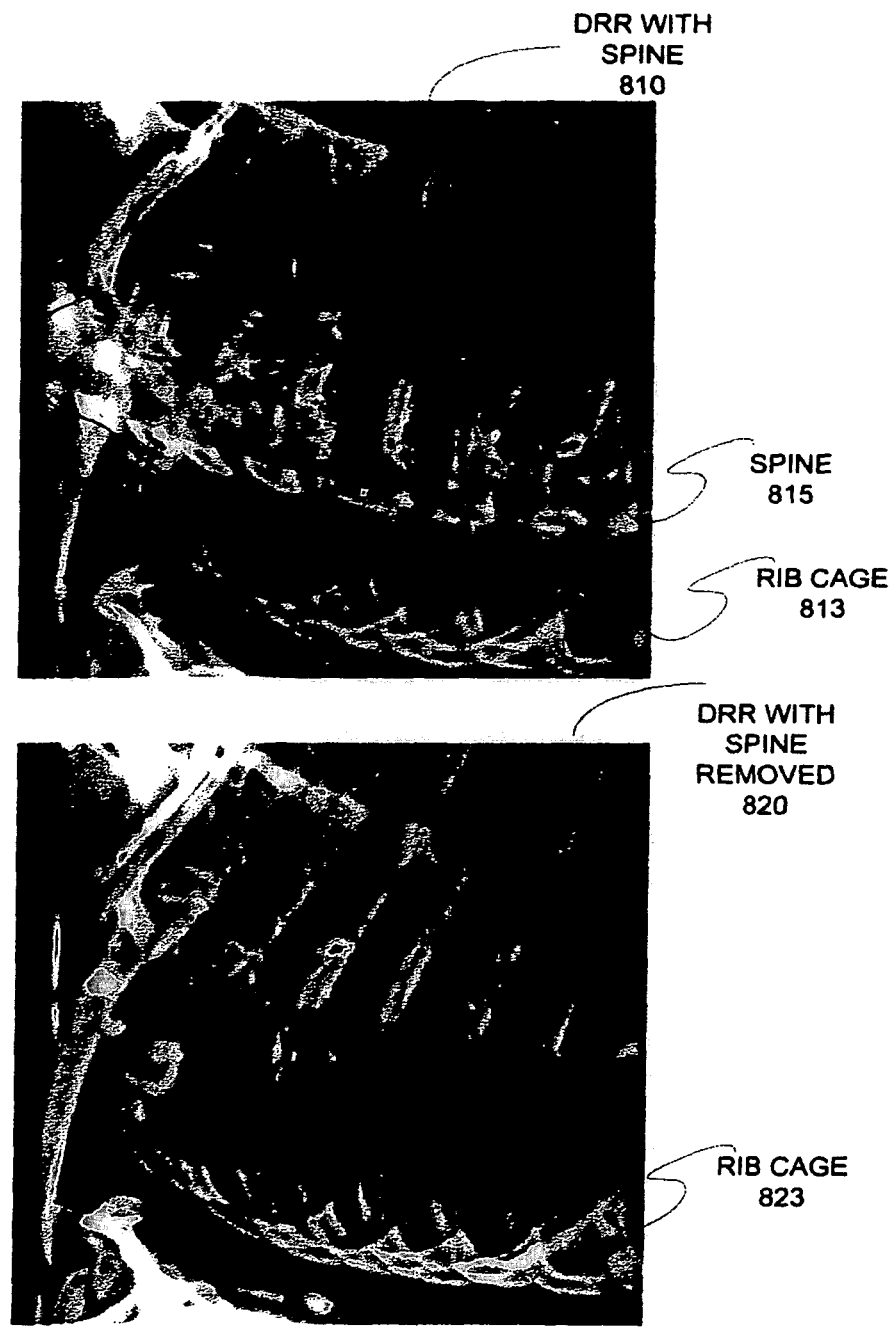
FIG. 8 illustrates some embodiments of digital reconstructed radiographs (DRRs).

FIG. 8 illustrates some embodiments of DRRs. The DRRs 810 and 820 may be generated from 4D CT images. The upper DRR 810 in FIG. 8 shows a section of a spine 815 as well as portions of a rib cage 813 of a patient. As mentioned above, the spine is a static bony structure, whereas the rib cage is a bony structure movable responsive to respiration of the patient. The lower DRR 820 in FIG. 8 shows substantially the same portions of the rib cage 823, but with the section of the spine segmented and removed. Embodiments of a process to segment and remove static bony structure have been described above. Since part of the spine 815 overlaps with part of the rib cage 813, the view of the rib cage 813 may be partially obstructed by the spine 815. Since the spine is removed from the lower DRR 820, the rib cage 823 in the lower DRR 820 may be viewed more clearly than the rib cage 813 in the upper DRR 810. As a result, it is easier to compare the lower DRR 820 with other intra-operative images showing about the same portion of the rib cage.

Thus, some embodiments of fiducial-less tracking of a VOI have been described. It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the treatment planning system, such as the application of a beam (e.g., radiation, acoustic, etc.) and "target" may refer to a non-anatomical object or area.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the present invention also relate to an apparatus for performing the operations herein. This apparatus may be specially constructed for the required purposes, or it may comprise a general-purpose computer selectively activated or reconfigured by a computer program stored in the computer. Such a computer program may be stored in a machine-readable storage medium, such as, but is not limited to, any type of disk including floppy disks, optical disks, CD-ROMs, and magnetic-optical disks, read-only memories (ROMs), random access memories (RAMs), erasable programmable ROMs (EPROMs), electrically erasable programmable ROMs (EEPROMs), magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the required method operations. The required structure for a variety of these systems will appear from the description below. In addition, embodiments of the present invention are not described with reference to any particular programming language. It will be appreciated that a variety of programming languages may be used to implement the teachings of embodiments of the invention as described herein.

In the foregoing specification, embodiments of the invention have been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method comprising:
generating, by a processing device, a plurality of digitally reconstructed radiograph (DRR) pairs from a plurality of volumes of four dimensional (4D) diagnostic imaging data showing a movable bony structure and a static bony structure of a patient, the generating comprising:
segmenting an image of the static bony structure from each of the plurality of volumes of 4D diagnostic imaging data, wherein the image of the static bony structure obstructs a view of the movable bony structure; and
removing the image of the static bony structure from the plurality of DRR pairs;
generating a pair of intra-operative images of a portion of the patient during treatment of a target region in the patient to show the movable bony structure of the patient, wherein the movable bony structure moves responsive to respiration of the patient;
comparing the pair of intra-operative images with the plurality of DRR pairs;
correlating a location of the movable bony structure in a particular volume of the plurality of volumes of 4D diagnostic imaging data with a location of the target region in the particular one of the plurality of volumes of 4D diagnostic imaging data, based on the comparing, to determine an intra-operative location of the target region in the patient using only the movable bony structure, wherein the 4D diagnostic imaging data shows the location of the target region; and
directing a treatment beam at the patient based on determining the intra-operative location of the target region.

2. The method of claim 1, further comprising:
defining a target region motion pattern based on locations of the target region in the plurality of volumes of 4D diagnostic imaging data, wherein the plurality of volumes of 4D diagnostic imaging data are captured at different intervals within a breathing cycle of the patient.

3. The method of claim 2, wherein the comparing the pair of intra-operative images with the plurality of DRR pairs comprises:
generating a similarity curve.

4. The method of claim 3, further comprising:
determining the intra-operative location of the target region at a time of the generating of the pair of intra-operative images based on the similarity curve and the target region motion pattern.

5. The method of claim 1, further comprising:
registering a spine of the patient to globally align the patient prior to beginning the treatment.

6. The method of claim 1, wherein the plurality of volumes of 4D diagnostic imaging data comprise a plurality of volumes of 4D computerized tomography (CT) data.

7. The method of claim 6, wherein the plurality of volumes of 4D CT data comprise a plurality of three-dimensional images, where each of the plurality of three-dimensional images represents a different point in a motion cycle.

8. A non-transitory machine-readable storage medium that provides instructions that, when executed by a processing device, performs operations comprising:
generating, by the processing device, a plurality of digitally reconstructed radiograph (DRR) pairs from a plurality of volumes of four dimensional (4D) diagnostic imaging data showing a movable bony structure and a static bony structure of a patient, the generating comprising:
segmenting an image of the static bony structure from each of the plurality of volumes of 4D diagnostic imaging data, wherein the image of the static bony structure obstructs a view of the movable bony structure; and
removing the image of the static bony structure from the plurality of DRR pairs;
generating a pair of intra-operative images of a portion of the patient during treatment of a target region in the patient to show the movable bony structure of the patient, wherein the movable bony structure moves responsive to respiration of the patient; and
comparing the pair of intra-operative images with the plurality of DRR pairs;
correlating a location of the movable bony structure in a particular volume of the plurality of volumes of 4D diagnostic imaging data with a location of the target region in the particular one of the plurality of volumes of 4D diagnostic imaging data, based on the comparing, to determine an intra-operative location of the target region in the patient using only the movable bony structure, wherein the 4D diagnostic imaging data shows the location of the target region; and
directing a treatment beam at the patient based on determining the intra-operative location of the target region.

9. The non-transitory machine-readable storage medium of claim 8, wherein the operations further comprise:
defining a target region motion pattern based on locations of the target region in the plurality of volumes of 4D diagnostic imaging data, wherein the plurality of volumes of 4D diagnostic imaging data are captured at different intervals within a breathing cycle of the patient.

10. The non-transitory machine-readable storage medium of claim 9, wherein the comparing the pair of intra-operative images with the plurality of DRR pairs comprises:
generating a similarity curve.

11. The non-transitory machine-readable storage medium of claim 10, wherein the operations further comprise:
determining the intra-operative location of the target region at a time of the generating of the pair of intra-operative images based on the similarity curve and the target region motion pattern.

12. The non-transitory machine-readable storage medium of claim 8, wherein the operations further comprise:
registering a spine of the patient to globally align the patient prior to beginning the treatment.

13. The non-transitory machine-readable storage medium of claim 8, wherein the plurality of volumes of 4D diagnostic imaging data comprise a plurality of volumes of 4D computerized tomography (CT) data.

14. The non-transitory machine-readable storage medium of claim 13, wherein the plurality of volumes of 4D CT data comprise a plurality of three-dimensional images, where each of the plurality of three-dimensional images represents a different point in a motion cycle.

* * * * *